United States Patent
Katou (10) Patent No.: US 8,858,438 B2
(45) Date of Patent: Oct. 14, 2014

(54) ULTRASOUND DIAGNOSTIC APPARATUS

(75) Inventor: Yoshiki Katou, Tokyo (JP)

(73) Assignee: Konica Minolta Medical & Graphic, Inc., Tokyo (JP)

(*) Notice: Subject to any disclaimer, the term of this patent is extended or adjusted under 35 U.S.C. 154(b) by 40 days.

(21) Appl. No.: 13/474,954

(22) Filed: May 18, 2012

(65) Prior Publication Data
US 2012/0302886 A1    Nov. 29, 2012

(30) Foreign Application Priority Data
May 26, 2011  (JP) .................................. 2011-117560

(51) Int. Cl.
*A61B 8/00*   (2006.01)
*A61B 8/08*   (2006.01)
*G06T 3/40*   (2006.01)
*G01S 7/52*   (2006.01)

(52) U.S. Cl.
CPC ............... *G06T 3/40* (2013.01); *G01S 7/52077* (2013.01); *A61B 8/5269* (2013.01)
USPC ........... 600/437; 600/407; 382/100; 382/276; 382/293; 382/294

(58) Field of Classification Search
USPC ........... 382/100, 276, 293, 294; 600/407, 437
See application file for complete search history.

(56) References Cited

U.S. PATENT DOCUMENTS 5,661,824 A * 8/1997 Allebach et al. ............... 382/298
2002/0133075 A1 * 9/2002 Abdelhak ..................... 600/443

FOREIGN PATENT DOCUMENTS

JP    8-299340    11/1996

* cited by examiner

*Primary Examiner* — Tse Chen
*Assistant Examiner* — Jason Ip
(74) *Attorney, Agent, or Firm* — Holtz, Holtz, Goodman & Chick PC (57) ABSTRACT

An ultrasound diagnostic apparatus including: an ultrasound probe to acquire a received signal via transmitting and receiving an ultrasound to and from a subject; an image generating section to generate an ultrasound image data based on the received signal acquired via said ultrasound probe; an output image generating section to generate output image data in such a manner that the output image data becomes a predetermined output size, by performing an image size changing process with respect to the ultrasound image data; a comparison image generating section to generate comparison image data by changing an image size of the output image data so that the comparison image data has an image size same as an image based on the ultrasound image data; and an image correction section to perform correction of the output image data, based on a difference between the comparison image data and the ultrasound image data.

3 Claims, 6 Drawing Sheets

ULTRASOUND DIAGNOSTIC APPARATUS

This application is based on Japanese Patent Application No. 2011-117560 filed on May 26, 2011, in Japan Patent Office, the entire content of which is hereby incorporated by reference.

TECHNICAL FIELD

The present invention relates to an ultrasound diagnostic apparatus.

BACKGROUND OF THE INVENTION

Conventionally, an ultrasound diagnostic apparatus is known which includes an ultrasound probe provided with an arrangement of a plurality of transducers, carries out scanning via an ultrasound beam with respect to a subject, such as a living body or the like, generates sound ray data sequentially from the received ultrasound, and generates and displays an ultrasound image based on the generated sound ray data.

In the case of the ultrasound diagnostic apparatus described above, for example, there is a heretofore known technique in which the value of interpolated data is determined in accordance with a difference between two echo data of the same depth on two adjacent ultrasound beams, and by forming a pseudo beam between the two ultrasound beams based on the determined value of interpolated data, the image size of an ultrasound image is changed (for example, this is described in Japanese Unexamined Patent Application Publication No. 08-299340).

However, in the case of the conventional technique described above, because there is a case in which accuracy of an image decreases when the image size of an ultrasound image is changed, resulted in a problem that the reliability of image decreases after changing the image size.

SUMMARY OF THE INVENTION

The present invention has been achieved in consideration of the above problems, and it is one of the main objects to provide an ultrasound diagnostic apparatus capable of improving accuracy of an image after changing the image size.

In order to solve at least one of the above objects, an ultrasound diagnostic apparatus reflecting one aspect of the present invention includes, but is not limited to: a) an ultrasound probe configured to acquire a received signal via receiving a reflected ultrasound from a subject while outputting a transmission ultrasound to the subject; b) an image generating section configured to generate an ultrasound image data based on the received signal acquired via the ultrasound probe; c) an output image generating section configured to generate an output image data in such a manner that the output image data becomes a predetermined output size, by performing an image size changing process with respect to the ultrasound image data having been generated via the image generating section; d) a comparison image generating section configured to generate a comparison image data by changing an image size of the output image data having been generated via the output image generating section so that the comparison image data has an image size identical to that of an image based on the ultrasound image data having been generated via the image generating section; and e) an image correction section configured to perform correction of the output image data, having been generated via the output image generating section, based on a difference between the comparison image data, having been generated via the comparison image generating section, and the ultrasound image data, having been generated via the image generating section.

Preferably, in the ultrasound diagnostic apparatus, the image correction section is configured to perform a correction of the output image data by a) changing processing conditions of the image size changing process via the output image generating section, based on the difference between the comparison image data, having been generated via the comparison image generating section, and the ultrasound image data, having been generated via the image generating section; and b) controlling the output image generating section to newly generate an output image data based on the processing conditions having been changed.

Preferably, the ultrasound diagnostic apparatus further includes, but is not limited to, a control section configured to set a number of times that generation of the comparison image data via the comparison image generating section and correction of the output image data via the image correction section are repeated, in accordance with predetermined transmission/reception conditions of ultrasound, wherein the generation of the comparison image data via the comparison image generating section and the correction of the output image data via the image correction section are repeated the number of times having been set via the control section.

Preferably, in the ultrasound diagnostic apparatus, the control section is configured to set the number of times that the generation of the comparison image data via the comparison image generating section and the correction of the output image data via the image correction section are repeated, in accordance with a depth of a predetermined focus point.

Preferably, the ultrasound diagnostic apparatus further includes, but is not limited to: a display section configured to display an image based on the output image data having been generated via the output image generating section; a setting input section configured to set a number of times that generation of the comparison image data via the comparison image generating section and correction of the output image data via the image correction section are repeated, in accordance with a predetermined operation performed via a user, and a control section configured to: a) perform a freeze control process, upon reception of a freeze operation, to maintain an image, according to a timing at which the freeze operation has been received, in a state in which the image is displayed in the display section; and b) repeat the generation of the comparison image data via the comparison image generating section and the correction of the output image data via the image correction section the number of times, having been set via the setting input section, with respect to an output image data of the image to be displayed in the display section according to the timing at which the freeze operation has been received.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DETAILED DESCRIPTION OF THE PREFERRED EMBODIMENTS

Hereinafter, a preferred embodiment for carrying out the present invention will be described with reference to the drawings. Although various limitations which are technically preferable for carrying out the present invention are accompanied to the following embodiment, scope of the invention is not limited to the following embodiment and the examples shown in the drawings.

Ultrasound diagnostic apparatus 20 is an apparatus which displays the condition of tissue inside a living organism of a patient (a subject) via an ultrasound image. In other words, ultrasound diagnostic apparatus 20 is configured to transmit ultrasound (transmission ultrasound) to the inside of a subject, such as a living organism, as well as to receive reflected waves of ultrasound (reflected ultrasound: echo) reflected from the inside of the subject. Ultrasound diagnostic apparatus 20 then converts the received reflected waves to electrical signals, and generates ultrasound image data based on the electrical signals. Ultrasound diagnostic apparatus 20 then displays the internal state of the subject as an ultrasound image based on the generated ultrasound image data. Also, ultrasound diagnostic apparatus 20 generates collateral information with respect to the generated ultrasound image data based on image capturing order information, and ultrasound diagnostic apparatus 20 is capable of generating an image file, based on prescribed standards, by attaching the collateral information to the ultrasound image data.

Figure 1:
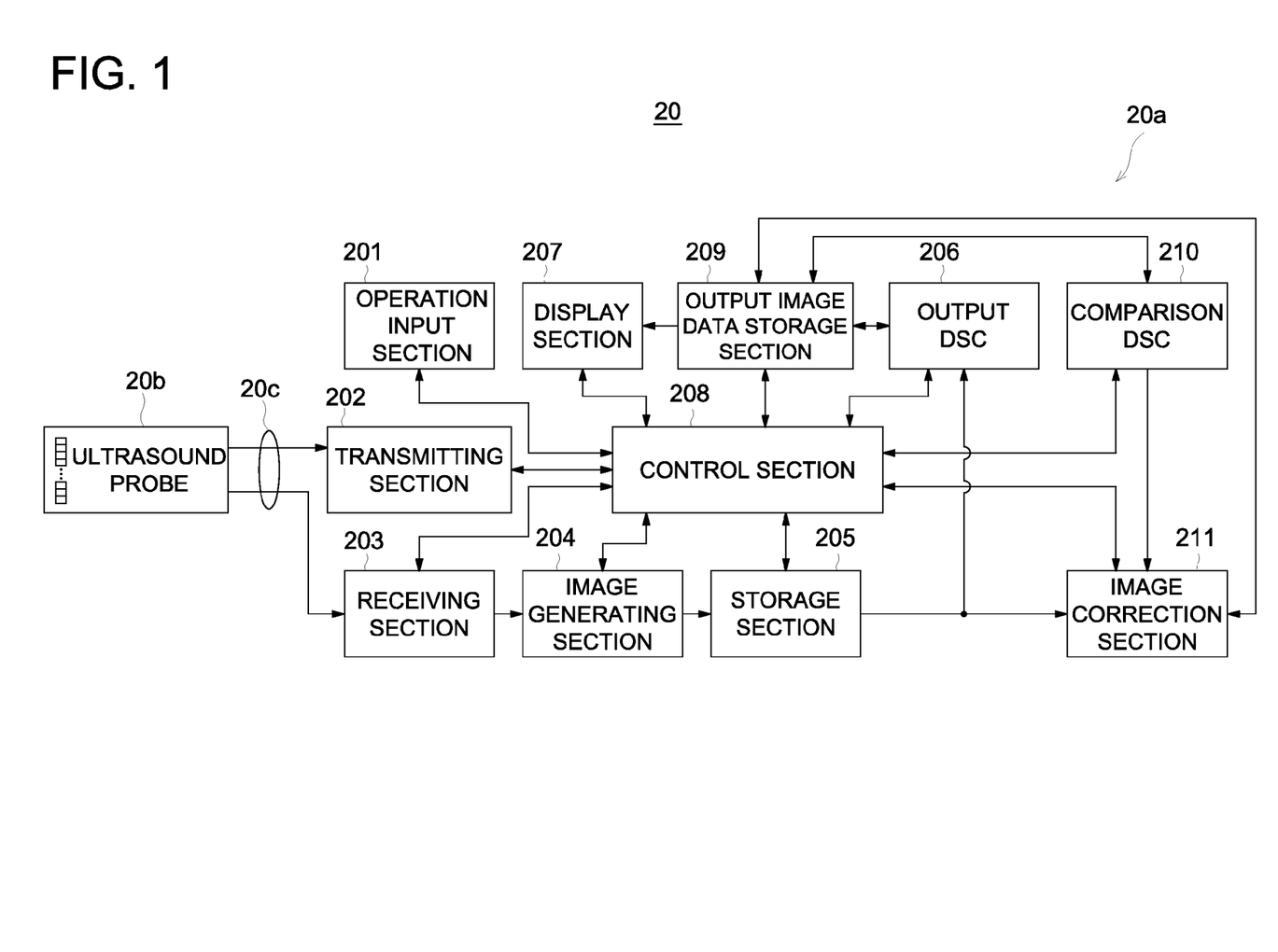
FIG. 1 is a block diagram illustrating a functional structure of an ultrasound diagnostic apparatus.

As illustrated in FIG. 1, ultrasound diagnostic apparatus 20 is provided with ultrasound diagnostic apparatus main-body 20a and ultrasound probe 20b. Ultrasound probe 20b is configured to transmit ultrasound, as well as to receive reflected waves, as described above. Ultrasound diagnostic apparatus main-body 20a is connected to ultrasound probe 20b via cable 20c, and controls ultrasound probe 20b to transmit a transmission ultrasound by transmitting a drive signal of electric signal to ultrasound probe 20b. Also, ultrasound diagnostic apparatus main-body 20a is configured to receive signals which are electric signals having been generated in ultrasound probe 20b in accordance with the reflected ultrasound from the inside of the subject, received by ultrasound probe 20b, and to generate ultrasound image data as described above.

Ultrasound probe 20b consists of a transducer (not illustrated in the figure) composed of a piezoelectric element. A plurality of these transducers is arranged in a one-dimensional array in an azimuth direction (scanning direction). In this preferred embodiment, as an example, ultrasound probe 20b consisting of 192 transducers is used. It should be noted that transducers may be arranged in a two-dimensional array. Also, the number of transducers may be set as appropriate. Furthermore, although a probe of a linear electronic scanning method is adopted in this preferred embodiment, another method such as an electric scanning method, or a mechanical scanning method may be adopted. Still further, another method such as a linear scanning method, sector scanning method, or convex scanning method may be adopted.

Ultrasound diagnostic apparatus main-body 20a is composed of; for example, but is not limited to, operation input section (setting input section) 201, transmitting section 202, receiving section 203, image generating section 204, storage section 205, output DSC (Digital Scan Converter) (output image generating section) 206, display section 207, control section 208, output image data storage section 209, comparison DSC (comparison image generating section) 210, and image correction section 211.

Operation input section 201 is composed of, for example, but is not limited to, a variety of switches, buttons, a trackball, a mouse, a keyboard, and the like, and configured to perform: input of a command which instructs the initiation of diagnosis, or data of individual information or the like of a subject; a freeze operation; input of a display enlarging operation for an enlarged-display in freeze control, or the like, and operation input section 201 outputs an operation signal to control section 208.

Specifically, as a user inputs the output size of an image into operation input section 201, the output size of the image is thereby set. Also, in a case in which an enlarged image is displayed by enlarging an image according to a freeze operation during the execution of a freeze control, as a user inputs a number of times of performing correction with respect to the enlarged image to operation input section 201, the number of times, of performing correction with respect to the enlarged image, is set.

Transmitting section 202 is a circuit configured to control ultrasound probe 20b to generate transmission ultrasound, by providing a drive signal, which is an electric signal, to ultrasound probe 20b via cable 20c, according to the control via control section 208. Also, transmitting section 202 is composed, for example, of a clock generating circuit, a delaying circuit, a pulse generating circuit. The clock generating circuit is a circuit configured to generate a clock signal which determines the transmission timing and transmission frequency of the drive signal. The delaying circuit is a circuit configured to set a delay time to the transmission timing of the drive signal for each individual pathway corresponding to each transducer, and to converge the transmission beams composed of transmission ultrasound by delaying the transmission of the drive signal by the delay time having been set. The pulse generating circuit is a circuit to generate a pulse signal as a drive signal in a predetermined cycle. Transmitting section 202, configured as described above, generates the transmission ultrasound, for example, by driving a continuous part (for example, 64 transducers) of a plurality of transducers (for example, 192 transducers). Then, transmitting section 202 performs scanning by shifting the transducer to be driven in an azimuth direction each time transmission ultrasound is generated.

Receiving section 203 is a circuit configured to receive signals, which are electric signals, from ultrasound probe 20b via cable 20c, according to the control via control section 208. Receiving section 203 is composed, for example, but is not limited to, of an amplifier, an A/D conversion circuit, and a beamforming circuit. The amplifier is a circuit configured to amplify the received signals with respect to each individual pathway corresponding to each transducer, by a predetermined amplification factor. The A/D conversion circuit is a circuit configured to perform an A/D conversion with respect to the amplified received signal. The beamforming circuit is a circuit to generate sound ray data by giving a delay time to each individual pathway, corresponding to each transducer, to adjust time phase with respect to the received signals, having been A/D converted, and by adding these received signals (phasing and addition).

Image generating section 204 is configured to carry out a logarithmic amplification process and an envelop detection process with respect to the sound ray data from receiving section 203, and to generate B-mode image data by carrying out luminance conversion after adjusting the dynamic range and gain. In other words, B-mode image data is data in which the intensity of a received signal is represented via luminance. Image generating section 204 may be configured in such a manner that, in addition to the B-mode image data, A-mode image data, M-mode image data, and image data via a Doppler method, can be generated.

Storage section 205 is composed of a semiconductor memory such as, for example, a DRAM (Dynamic Random Access Memory) and the like, and configured to store the B-mode image data, transmitted from image generating section 204, frame by frame. In other words, it is possible to store the B-mode image data as frame image data. Then, the frame image data, having been stored, is transmitted to output DSC 206 and image correction section 211, according to the control via control section 208. Storage section 205 is composed of a large capacity memory which is capable of storing frame image data of approximately 10 seconds, and, for example, the most recent 10 seconds of frame image data is stored via a FIFO (First-In First-Out) method.

Output DSC 206 is configured to carry out, as an output generating section, coordinate transformation to transform the frame image data, received from storage section 205, into image data by the scanning method of a television signal, as well as to generate output image data by performing an image size changing process so that the output image data becomes the output size, having been set via operation input section 201. Output DSC 206 transmits the output image data, having been generated, to output image data storage section 209.

Specifically, output DSC 206 is configured to change image size by performing a magnification interpolation process, such as linear interpolation, bi-linear interpolation, cubic interpolation, nearest-neighbor interpolation, and the like, as an image size changing process, with respect to image data so that the image data becomes the output size having been set via operation input section 201.

Figure 4:
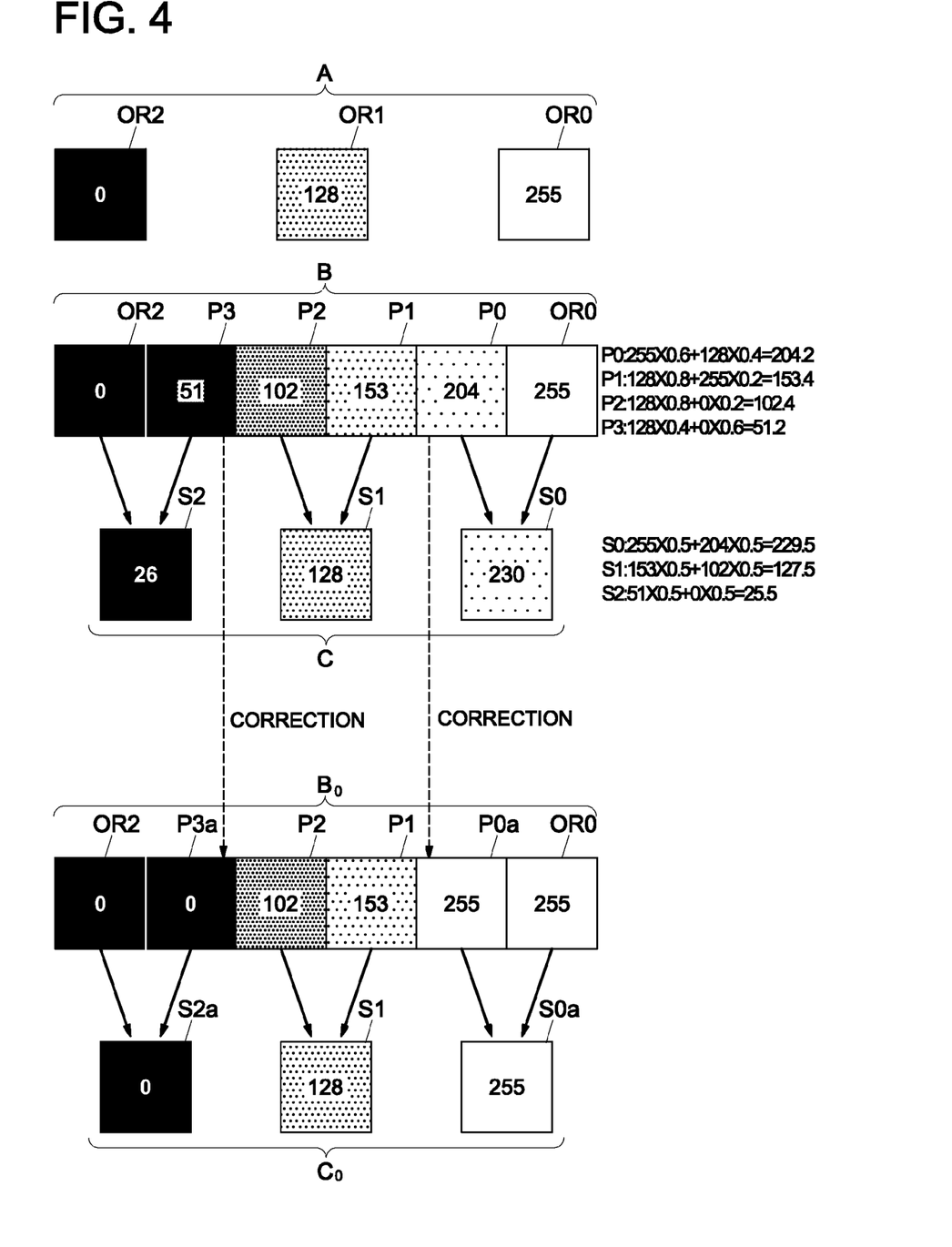
FIG. 4 is a diagram explaining change of an image size.

It should be noted that output DSC 206 may instead perform a reduction interpolation process with respect to image data. Here, reduction interpolation process is a process in which one pixel data is generated from some of pixel data of the pixel data which constitute the image data, and the total number of pixel data is reduced, as illustrated in FIG. 4 as an example.

As display section 207, a display device such as a LCD (Liquid Crystal Display), a CRT (Cathode-Ray Tube) display, an organic EL (Electronic Luminescence) display, an inorganic EL display, a plasma display, or the like, can be applied. Display section 207 is configured to display an image on a display screen based on output image data transmitted from output image data storage section 209. It is to be noted that it may be configured in such a way that printed output is possible by applying a printing device, such as a printer, instead of a display device.

Control section 208 is constituted, for example, but is not limited to, of CPU (Central Processing Unit), ROM (Read Only Memory), RAM (Random Access Memory), and is configured to read out a variety of process programs, such as a system program and the like, having been stored in ROM, and to expand the programs into RAM, to integrally control the operation of each section of ultrasound diagnostic apparatus 20 in accordance with the expanded programs.

ROM is constituted of non-volatile memory and the like of semiconductors or the like, and stores a system program corresponding to ultrasound diagnostic apparatus 20, various types of process programs, which can be executed on the system program, such as, for example, a program to execute an auto-scanning process or the like, and various types of data and the like such as a gamma table or the like. These programs are stored in a form of program codes which can be read by a computer, and the CPU sequentially executes the operations according to the program codes.

RAM forms a work area in which various types of programs to be executed by the CPU and data according to the programs are temporarily stored.

Specifically, control section 208 sets the number of times that generation of comparison data via comparison DSC 210, and correction of output image data via output image correction section 211 are repeated in accordance with predetermined transmission/reception conditions of ultrasound, in other words, control section 208 sets the number of times of performing correction with respect to output image data.

Also, when control section 208 has received a freeze operation via operation input section 201, control section 208 carries out a freeze control to maintain a state in which an image, according to the timing at which control section 208 has received the freeze operation, is displayed in display section 207.

Output image data storage section 209 is constituted in a similar fashion as storage section 205, and is configured to store output image data, having been generated after having been subjected to a coordinate transformation process and an interpolation process via output DSC 206, frame by frame. Then, the output image data, having been stored, is transmitted to display section 207, comparison DSC 210, and image correction section 211, in accordance with the control via control section 208.

Comparison DSC 210 is configured, as a comparison image generating section, to generate comparison image data by changing the image size of output image data, received from output image data storage section 209, so that the output image data has an image size identical to that of the frame image data generated via image generating section 204. Comparison DSC 210 transmits the generated comparison image data to image correction section 211.

Specifically, comparison DSC 210 changes the image size by performing a magnification interpolation process or a reduction interpolation process with respect to output image data, in a similar fashion as output DSC 206. It should be noted that changes of image size via output DSC 206 and changes of image size via comparison DSC 210 are irreversible.

Image correction section 211 is configured to compare frame image data, having been received from storage section 205, with comparison image data, having been received from comparison DSC 210, pixel data by pixel data, and detects a difference between the two image data. Image correction section 211 performs correction of output image data, having been received from output image data storage section 209, based on the detected difference.

Specifically, image correction section 211 is configured to set a correction value in such a manner that the detected difference, resulting from the comparison of the image data, approaches zero, and to perform correction with respect to interpolation pixel data of output image data based on the set correction value. It should be noted that image correction section 211 may be configured to change the correction value in accordance with the number of times of corrections.

Also, image correction section 211 may be configured to change process conditions of the image size changing process via output DSC 206, and to perform correction of output image data by controlling output DSC 206 to newly generate output image data based on the process conditions having been changed.

Next, an image display process to be executed by ultrasound diagnostic apparatus 20, which is constituted as described above, will be described with reference to FIGS. 2 through 4.

Figure 2:
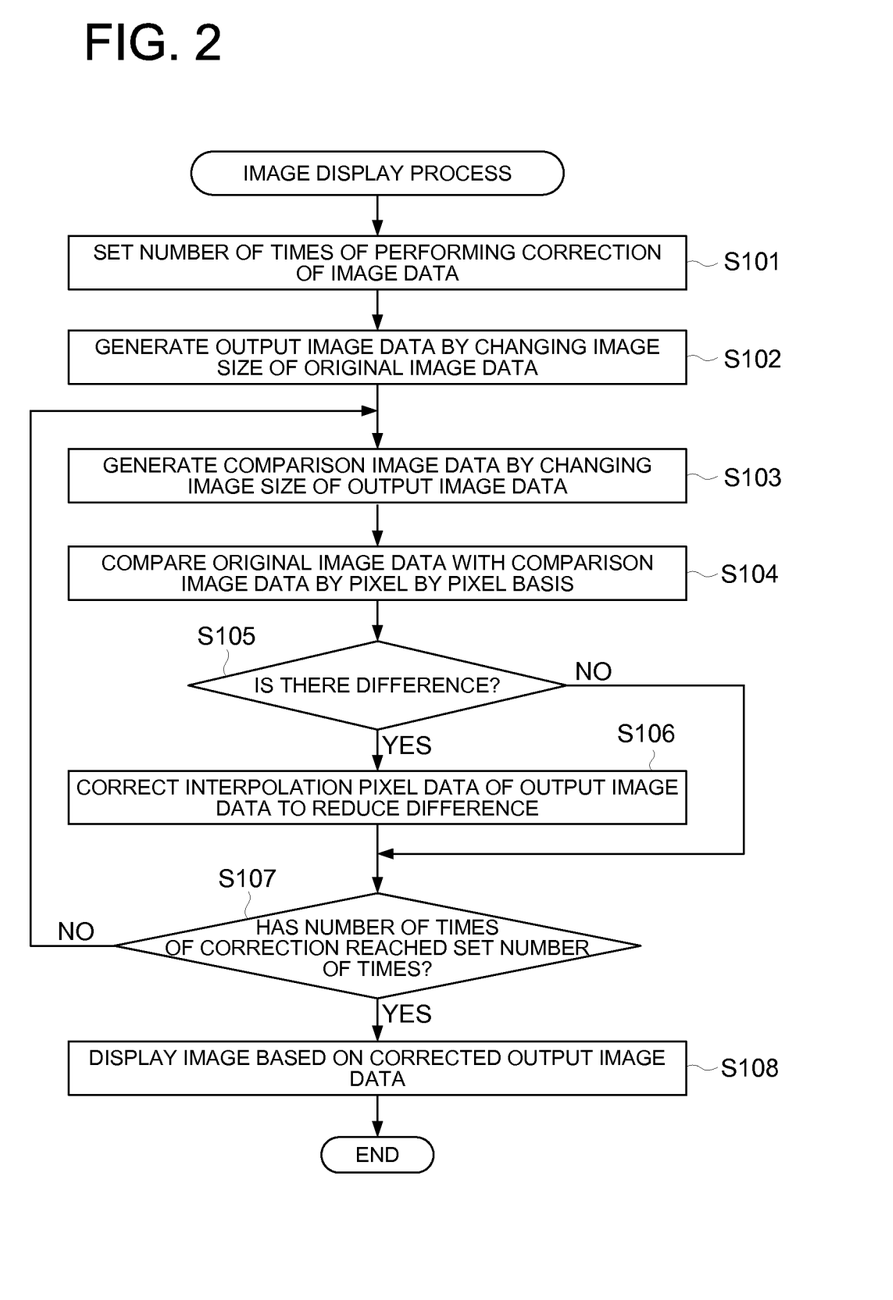
FIG. 2 is a flowchart depicting an exemplary flow of an image display process.

First, control section 208 sets a frame rate based on predetermined transmission/reception conditions of ultrasound, and sets the number of times of performing correction according to the frame rate (step S101).

The predetermined transmission/reception conditions of ultrasound are various conditions which influence the time required for generating image data, such as, for example, the density of scanning lines, a width of a visual field, a number of transducers of an ultrasound probe, a depth of a focus point, a number of emissions of a transmission beam (in cases in which a pulse inversion and multiple focusing are carried out, or the like), and the like. Because the time required for generating the image data changes in accordance with the predetermined transmission/reception conditions of ultrasound, control section 208 sets a frame rate in display section 207 according to the conditions of transmission/reception of ultrasound. Control section 208, which has stored the values of frame rate and the numbers of corrections by correlating to each other in the ROM, sets the number of times of performing correction by extracting the number of times of corrections correlated to the frame rate, which has been set according to the transmission/reception conditions of ultrasound.

Here, how the frame rate depends on the transmission/reception conditions of ultrasound will be described in detail.

As an ultrasound diagnostic apparatus in recent years, an ultrasound diagnostic apparatus has become common in which multiple focusing, which carries out a plurality of transmissions of ultrasound, is performed while changing the depth of a transmission focus point in one direction. In cases in which multiple focusing is performed, scanning for the number of points of transmission focus is carried out in one frame. In other words, in the case in which an ultrasound probe, wherein 192 transducers are arranged, for example, is used, 192 times of transmission beams are emitted in one scanning, and in one frame, transmission beams are emitted for the number of times of multiplication between the number of times of transmission beams in one scanning and the number of points of transmission focus. The time required for one transmission/reception of ultrasound becomes greater in proportion to the depth of the transmission focus point. Also, it is necessary to set a constant waiting time each time when a transmission beam is emitted, in order to avoid a mixture of a transmission ultrasound and a reflected ultrasound. Therefore, although a higher quality ultrasound image can be acquired as the depth and the number of the transmission focus point increase, the time required for acquiring the image increases. In other words, the frame rate decreases.

Also, some ultrasound diagnostic apparatuses in recent years are provided with functions to display an ultrasound image by carrying out THI (Tissue Harmonic Imaging). THI is a technique in which a fundamental wave is output and a secondary harmonic wave, which has twice the frequency of the fundamental wave, resulting from distortion of the fundamental wave in the subject, is received, and an ultrasound image is generated based on the secondary harmonic wave, and it is a technique to seek reduction in artifact. In the case of generating an ultrasound image via THI, since it is necessary to remove the fundamental wave included in the reflected ultrasound, pulse inversion is carried out in which an ultrasound which possesses a waveform opposite in phase from that of the fundamental wave is further transmitted to erase the component of the fundamental wave. In this case, it is necessary to further transmit an ultrasound twice the number of times, resulting in a further decrease of the frame rate.

Figure 3:
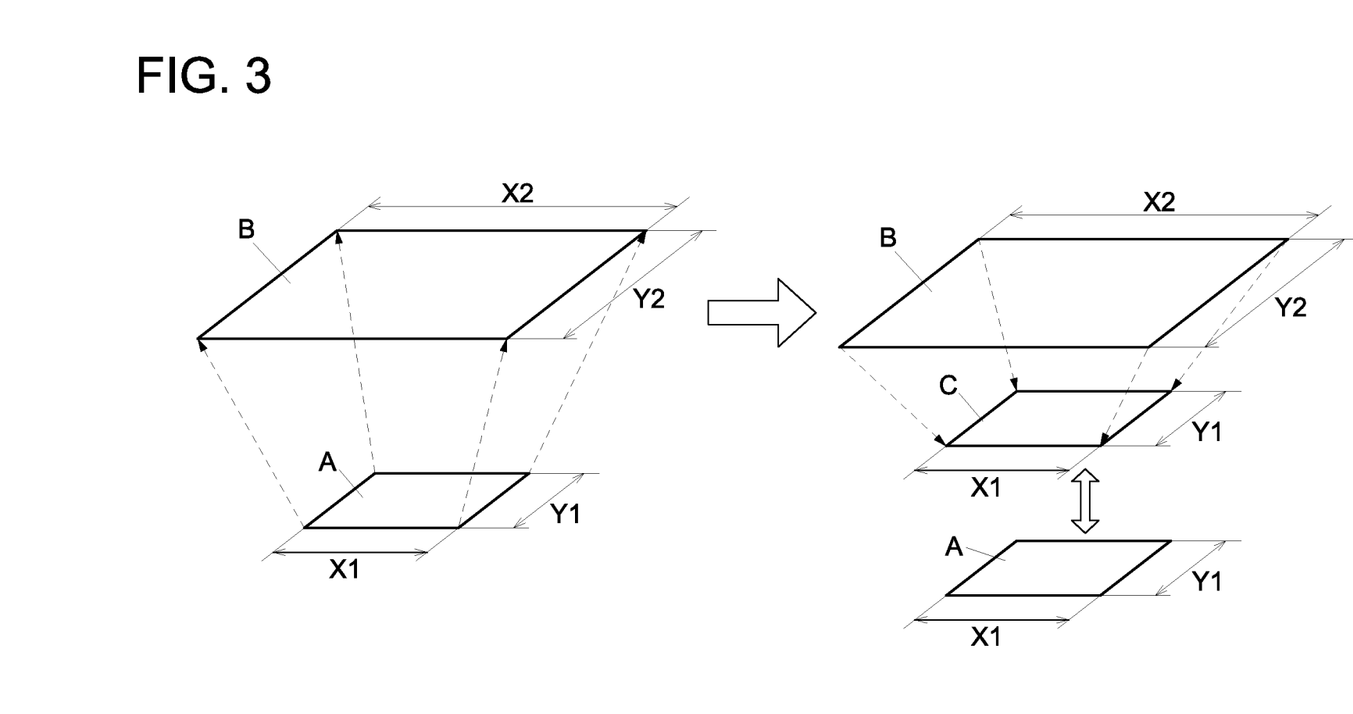
FIG. 3 is a diagram explaining change of an image size.

Next, control section 208 reads out frame image data (hereinafter, referred to as original image data A) which has been stored in storage section 205, and transmits the frame image data to output DSC 206. Output DSC 206 performs an image size changing process with respect to original image data A of an image size of X1×Y1 to have a desired output size of X2×Y2, as illustrated in FIG. 3 for example, and generates output image data B of an image size of X2×Y2 (step S102). Specifically, assuming that original image data A includes pixel data OR0, OR1, and OR2, for example as illustrated in FIG. 4, output DSC 206 performs a magnification interpolation process, as an image size changing process, with respect to original image data A, and generates output image data B which includes pixel data OR0 and OR2 and interpolation pixel data P0, P1, P2, and P3. The generated output image data B is transmitted to output image data storage section 209 via output DSC 206, and stored in output image data storage section 209.

Next, control section 208 reads out output image data B, having been stored in output image data storage section 209, and transmit the output image data to comparison DSC 210. Comparison DSC 210 changes the image size of output image data B so that the image size becomes an image size of X1×Y1 which is identical to that of original image data A, and generates comparison image data C of an image size of X1×Y1 (step S103). Specifically, comparison DSC 210 performs a reduction interpolation process with respect to output image data B which includes pixel data OR0 and OR2 and interpolation pixel data P0, P1, P2, and P3, as illustrated in FIG. 4 for example, and generates comparison image data C which includes pixel data S0, S1, and S2. Comparison image data C, having been generated, is transmitted to image correction section 211 via comparison DSC 210.

Next, control section 208 reads out original image data A, having been stored in storage section 205, and transmits the original image data to image correction section 211. Image correction section 211 compares the received original image data A with comparison image data C on a pixel by pixel basis, and detects a difference therebetween (step S104). Specifically, as illustrated in FIG. 4 for example, image correction section 211 compares each pixel value of pixel data OR0, OR1, and OR2 of original image data A with each pixel value of pixel data S0, S1, and 52 of comparison image data C, and determines whether or not there is a difference between pixel values.

Next, control section 208 determines whether or not a difference between pixels of original image data A and comparison image data C has been detected via image correction section 211 (step S105). Specifically, as illustrated in FIG. 3 for example, when comparing each pixel value of pixel data OR0, OR1, and OR2 of original image data A and each pixel value of pixel data S0, S1, and S2 of comparison image data C, although the pixel value of pixel data OR1 corresponds to the pixel value of pixel data S1, a difference occurs between the pixel value of pixel data OR0 and the pixel value of pixel data S0, and a difference also occurs between the pixel value of pixel data OR2 and the pixel value of pixel data S2. Therefore, in the case illustrated in FIG. 4, image correction section 211 detects the difference between the pixels of original image data A and comparison image data C, and it is determined that a difference has been detected via control section 208.

In cases in which it has been determined that a difference has been detected (step S105: YES), control section 208 reads out output image data B, having been stored in output image data storage section 209, and transmits the data to image correction section 211, after which image correction section 211 corrects output image data B based on the detected difference (step S106). Specifically, as illustrated in FIG. 4 for example, image correction section 211 increases or decreases the pixel values of interpolation data P0 and P3, which constitutes output image data B, by a constant value so that the difference between each pixel value of pixel data OR0, OR1, and OR2 of original image data A and the pixel value of pixel data S0, S1, and S2 of comparison image data C decreases. In such a way, output image data B is corrected to output image data $B_0$ which includes pixel data OR0 and OR2 and interpolation pixel data P0a, P1, P2, and P3a.

Control section 208 transmits corrected output image data $B_0$, after having been corrected via image correction section 211, to output image data storage section 209, and overwrites output image data B, having been stored in output image data storage section 209, with output image data $B_0$, after having been corrected.

It should be noted that in cases in which it is determined that a difference has been detected (step S105: YES), as a method to correct output image data B, in addition to the method in which output image data B is corrected by correcting interpolation pixel data as described above, examples of a method include a method in which process conditions for image size changing process via output DSC 206 is changed based on the detected difference, and output image data B is corrected by generating output image data $B_0$ via output DSC 206 based on the process conditions which have been changed.

In cases in which it is determined that no difference has been detected (step S105: NO), control section 208 omits the process in step S106, and carries out the process in step S107.

Next, control section 208 determines whether or not the number of times of corrections, having been performed with respect to output image data B via image correction section 211, has exceeded the number of times which has been set in step S101 (step S107). Here, even if no difference has been detected in step S105 and therefore the process to be carried out in step S106 is omitted, this omission is to be included in "the number of times the correction has been performed" in step S107.

In cases in which the number of times of corrections has not reached the number of times which has been set (step S107: NO), control section 208 carries out the processes in step S103 through step S107 again. In other words, control section 208 transmits output image data $B_0$, after having been subjected to a correction via image correction section 211 in step S106, to comparison DSC 210, after which comparison DSC 210 generates comparison image data $C_0$ by changing the image size of output image data $B_0$, after having been corrected, so that the image size becomes the same as that of original image data A, and carries out the subsequent processes in step S104 through step S107 again.

On the other hand, in cases in which it has been determined that the number of times of corrections has reached the number of times having been set (steps S107: YES), control section 208 reads out output image data $B_0$, after having been corrected and stored in output image data storage section 209, and controls display section 207 to display the data.

Following the above, the image display process is complete.

It should be noted that although an example case, in which a difference between original image data and each pixel of comparison image data is eliminated via single correction, is depicted in FIG. 4, a difference between original image data and comparison image data may be reduced gradually via multiple corrections.

Figure 5:
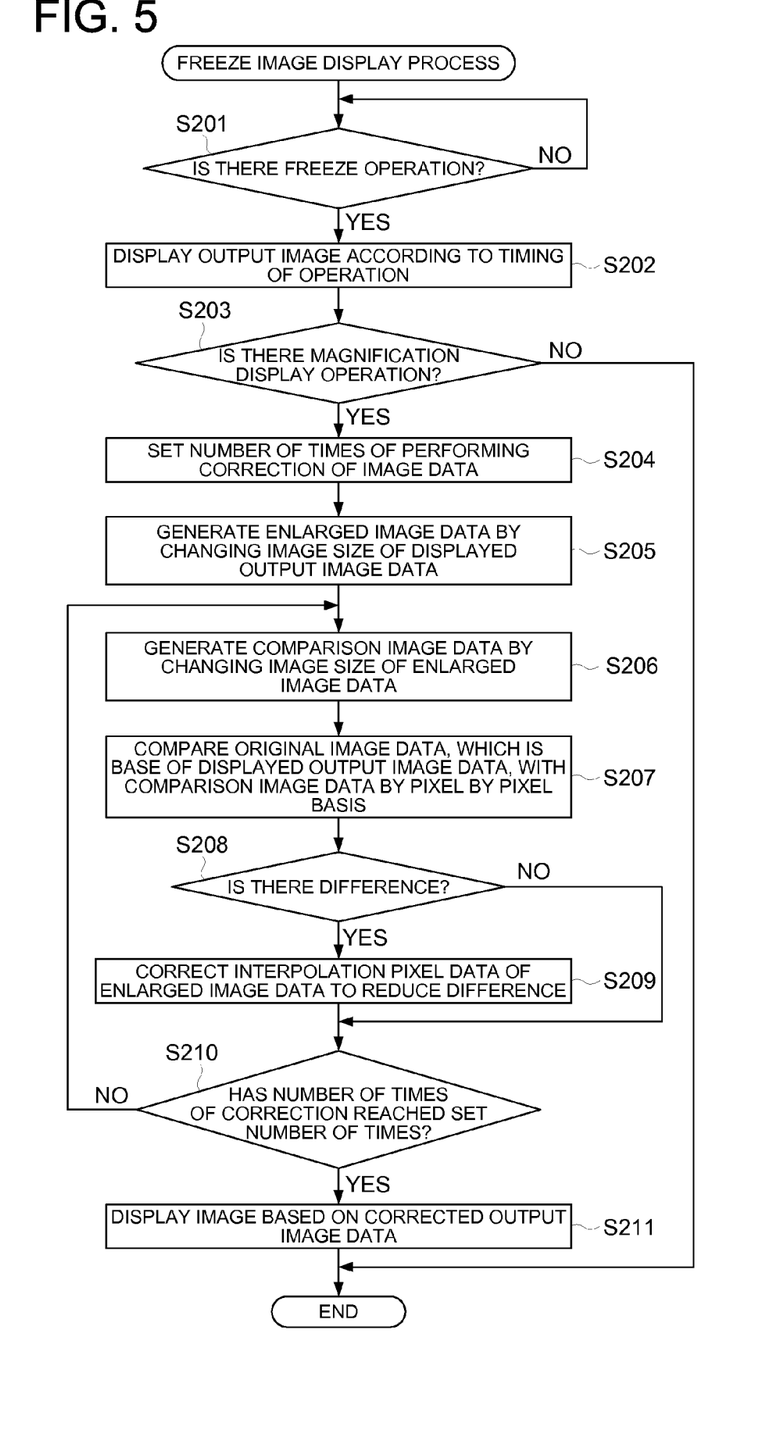
FIG. 5 is a flowchart depicting an exemplary flow of a freeze image display process.

Also, a freeze image display process, to be executed by ultrasound diagnostic apparatus 20 which is constituted as described above, will now be described with reference to FIG. 5. This freeze image display process is a process which is to be executed in a case in which a freeze operation is carried out by the user while output images are displayed sequentially in display section 207 after the above described correction process has been executed.

First, control section 208 determines whether or not a freeze operation has been input via operation input section 201 (step S201).

When it is determined that a freeze operation has been input (step S201: YES), control section 208 initiates the freeze control to maintain the state in which an output image, according to the timing at which the freeze operation was received, is displayed on a display screen in display section 207 (step S202).

Next, control section 208 determines whether or not a magnification display operation has been input via operation input section 201 (step S203). Here, the magnification display operation is a magnification ratio designating operation to display the output image, displayed in display section 207 according to the timing at which the freeze operation was received, in an enlarged view at a desired magnification ratio.

In cases in which it is determined that a magnification display operation has been input (step S203: YES), control section 208 sets the number of times of performing correction in accordance with the value which has been input via operation input section 201 (step S204). Here, in the freeze image display process, because a correction is performed with respect to a still image of which the image size has been enlarged, the number of times of performing correction is not set according to the frame rate, but the number of times of performing correction is set according to the value having been set by the user.

It should be noted that, in cases in which it is determined that no magnification display operation has been input (step S203: NO), control section 208 completes the freeze image display process.

Next, control section 208 reads out output image data (hereinafter referred to as output image data D) of an output image to be displayed in display section 207 in accordance with the timing at which the freeze operation has been received, from output image data storage section 209, and transmits the output image data to output DSC 206. Output DSC 206 carries out an image size changing process with respect to output image data D so as to be displayed in an enlarged view at the magnification ratio designated in step S203, and generates an enlarged image data (hereinafter referred to as enlarged image data E) (step S205). Enlarged image data E, having been generated, is transmitted to output image data storage section 209 via output DSC 206, and stored in output image data storage section 209.

Next, control section 208 reads out enlarged image data E, having been stored in output image data storage section 209, and transmits the enlarged image data to comparison DSC 210. Comparison DSC 210 changes the image size of enlarged image data E so that the image size becomes the same image size as that of frame image data (hereinafter referred to as original image data F) based on which output image data D has been generated, in the image display process depicted in FIG. 2, and generates comparison image data (hereinafter referred to as comparison image data G) (step S206). Comparison image data G, having been generated, is transmitted to image correction section 211 via comparison DSC 210.

Next, control section 208 reads out original image data F, having been stored in storage section 205, and transmits the original image data to image correction section 211. Image correction section 211 compares original image data F, having been received, with comparison image data G on a pixel by pixel basis, and detects a difference (step S207).

Next, control section 208 determined whether or not a difference between pixels of original image data F and comparison image data G has been detected via image correction section 211 (step S208).

In cases in which it is determined that a difference has been detected (step S208: YES), control section 208 reads out enlarged image data E, having been stored in output image data storage section 209, and transmits that data to image correction section 211, and image correction section 211 corrects enlarged image data E based on the detected difference (step S209).

Control section 208 transmits the corrected enlarged image data $E_O$, after having been corrected via image correction section 211, to output image data storage section 209, and overwrites enlarged image data E, having been stored in output image data storage section 209, with enlarged image data $E_O$, after having been corrected.

It should be noted that, in cases in which it has been determined that no difference has been detected (step S208: NO), control section 208 omits the process in step S209, and carries out the process in step S210.

Next, control section 208 determines whether or not the number of times of corrections, having been performed with respect to enlarged image data E via image correction section 211, has exceeded the number of times which has been set in step S204 (step S210).

In cases in which the number of times of corrections does not reach the number of times which has been set (step S210: NO), control section 208 carries out the processes in step S206 through step S210 again.

On the other hand, in cases in which it has been determined that the number of times of corrections has reached the number of times having been set (steps S210: YES), control section 208 reads out the enlarged image data, having been stored in output image data storage section 209, and controls display section 207 to display the data.

Following the above, the freeze image display process is complete.

It should be noted that the freeze image display process is complete when a freeze control completion operation has been received via operation input section 201, or a predetermined time, which has been prescribed in advance, has elapsed.

As described above, according to this preferred embodiment, output image data is generated by changing the image size of a frame image data so as to become a desired output size, and generates a comparison image data by changing the image size of the output image data so as to become the same image size of that of the frame image data, and corrects the output image data based on the difference between the frame image data and the comparison image data, and therefore, the accuracy of an output data, after changing the image size, can be improved. Thus, the reliability of an output image, after changing the image size, can be improved.

Also, because the number of times that generation of comparison image data and correction of an output image data are repeated (the number of times of performing correction) is set in accordance with predetermined transmission/reception conditions of ultrasound, and the generation of a comparison image data and correction of an output image data are repeated the number of times having been set, a multiple times of corrections can be performed with respect to an output image in an ultrasound diagnostic apparatus in which the frame rate decreases significantly according to transmission/reception conditions of ultrasound, and therefore, an output image having a higher image quality can be displayed in accordance with lowness of a frame rate.

Also, because the number of times of performing correction with respect to image data is set in accordance with the depth of a focus point, the number of times of performing correction increases as the depth of a focus point increases, and therefore, an output image having a higher image quality can be displayed.

Also, because the number of times that generation of comparison image data and correction of output image data (the number of times of performing correction) with respect to an image, which is displayed in display section 207 according to the timing at which a freeze operation is received, is set in accordance with the operation via operation input section 201, the number of times of performing correction can be set in concert to a taste of user and/or diagnosis positions, and therefore, a freeze image having a higher image quality, according to need, can be displayed.

It should be noted that, although an image which is based on output image data and enlarged image data, having been stored, is outputted in a display section in an ultrasound diagnostic apparatus in this preferred embodiment, said image data may be output to a display apparatus or a printing apparatus which is connected externally to the ultrasound diagnostic apparatus, or output to an external device connected via a network or the like.

Also, the above described image correction is performed with respect to all of the frame data generated via an image generating section in this preferred embodiment, an image correction process may be performed, as appropriate, for example, only in a case in which a prescribed operation has been carried out via an operation input section.

Further, although a reduction interpolation process is carried out with respect to image data in a case in which an image size is to be reduced in this preferred embodiment (refer to FIG. 4), the image size may be changed by removing a part of pixel data.

Also, although output image data (or enlarged image data) is generated by changing the image size by carrying out a magnification interpolation process with respect to original image data in this preferred embodiment (refer to FIG. 3), output image data may be generated by changing the image size by carrying out a magnification interpolation process with respect to original image data only in a transverse direction (in an azimuth direction), or output image data may be generated by changing the image size by carrying out a magnification interpolation process with respect to frame image data in a transverse direction (in an azimuth direction) and by carrying out a reduction interpolation process in a longitudinal direction (in a depth direction).

Furthermore, although an enlarged image, having been corrected after having been subjected to corrections of the number of times having been set, is displayed in a display section in a freeze image display process in this preferred embodiment, an enlarged image having been corrected each time a single correction is performed may be displayed in a display section.

Also, although an example is disclosed in which a hard disk, a non-volatile memory of a semiconductor, or the like, is used as a computer-readable medium of the programs according to the present invention in this preferred embodiment, the medium is not limited to the examples. As another computer-readable medium, a portable recording medium such as a CD-ROM may be applied. Also, as a medium to provide the data of the programs according to the present invention, a carrier wave may be applied.

EXAMPLE 1

Figure 6:
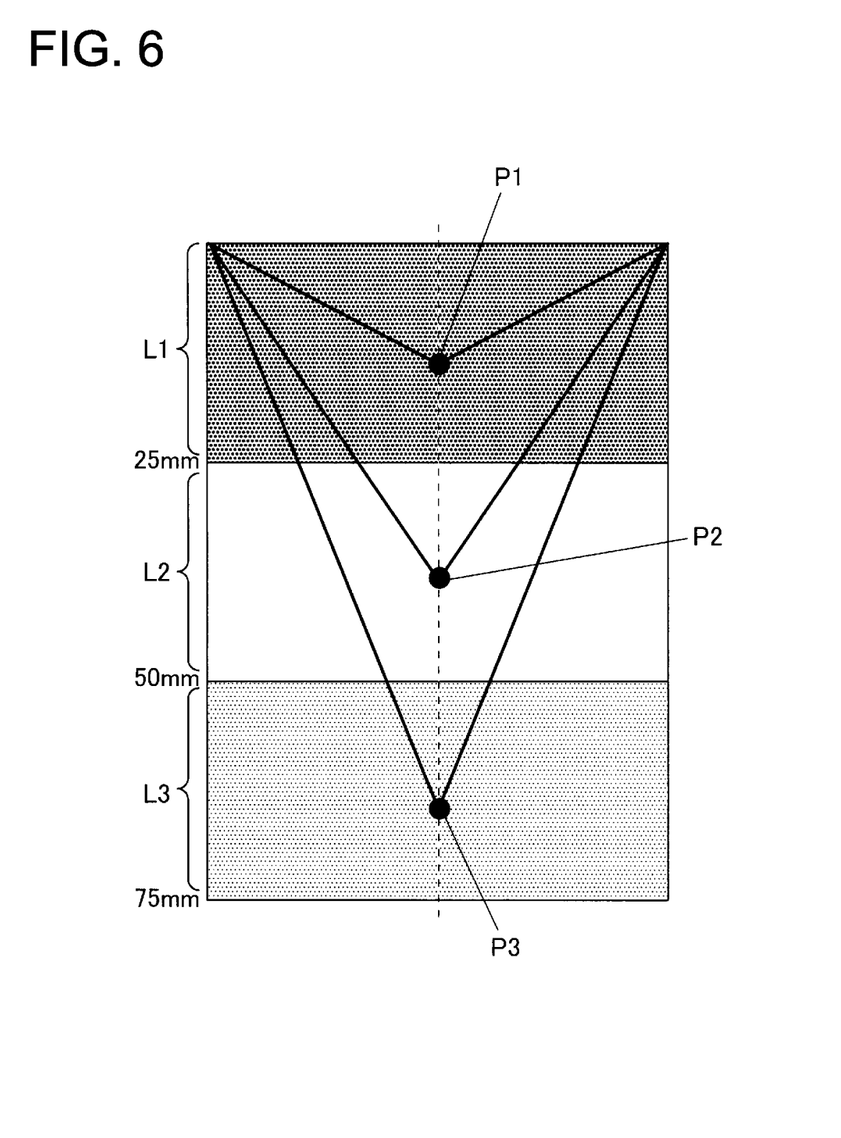
FIG. 6 is a diagram explaining a case in which a multiple focusing is carried out.

In ultrasound diagnostic apparatus 20 according to this preferred embodiment, the time required for generating frame image data in a case in which a multiple focusing is carried out with reference to FIG. 6.

It is to be noted that, in this preferred embodiment, as illustrated in FIG. 6, a case will be described in which sound ray data, in area L1 from depth 0 mm (the surface of a subject) to depth 25 mm, is acquired by setting the depth of a focus point to position P1, and then sound ray data, in area L2 from depth 25 mm to depth 50 mm, is acquired by setting the depth of the focus point to position P2, then following that, sound ray data, in area L3 from depth 50 mm to depth 75 mm, is acquired by setting the depth of the focus point to position P3.

Assuming that the velocity of sound is 1,540 m/s in a subject, the time required for acquiring sound ray data in area L1 is $25 \times 10^{-3} \times 2/(1{,}540 \times 10^{-3}) = 0.0324675$ ms, and the time required for acquiring sound ray data in area L2 is $5 \times 10^{-3} \times 2/(1{,}540 \times 10^{-3}) = 0.0649351$ ms, and the time required for acquiring sound ray data in area L3 is $75 \times 10^{-3} \times 2/(1{,}540 \times 10^{-3}) = 0.0974026$ ms. Here, the time which is about 1.5 times as large as the time required for acquiring the sound ray data in each area is conventionally necessary so that the transmission/reception of ultrasound at a focus point has no influence on the transmission/reception of ultrasound at other focus points. Therefore, the time required for acquiring the data of a single sound ray becomes $0.0324675 \times 1.5 + 0.0649531 \times 1.5 + 0.0974026 \times 1.5 = 0.2922078$ (ms). In a case in which the data of 192 sound ray are to be acquired, the time required for generating an image for a single frame becomes $0.2922078 \times 192 = 56.1038976$ (ms).

Therefore, in a case in which a multiple focusing, like this preferred embodiment, is carried out, the frame rate of the ultrasound diagnostic apparatus becomes about 18 fps (1/0.0561038976=17.824104).

Since the frame rate of a commercially available television receiver is about 60 fps, the frame rate of the ultrasound diagnostic apparatus according to the preferred embodiment is about ⅓ or less than that of a commercially available television receiver. Although only about one correction of output image data can be per formed in cases in which the frame rate is about 60 fps, the same as that of a commercially available television receiver, multiple times of corrections of output image data can be performed in the above described image display process in the case of this preferred embodiment. In this way, since the frame rate of an ultrasound diagnostic apparatus decreases significantly according to transmission/reception conditions of ultrasound, a multiple times of corrections with respect to output image data can be performed in the ultrasound diagnostic apparatus according to the preferred embodiment of the present invention.

Although the preferred embodiment of the present invention has been described by way of the accompanying drawings, it should be noted that specific structures are not restricted to those shown in the embodiments. Various changes and modifications should be construed as being contained in the present invention unless such changes and modifications depart from the scope of the present invention.

What is claimed is:

1. An ultrasound diagnostic apparatus comprising:
   an ultrasound probe which outputs a transmission ultrasound to a subject, and which acquires a received signal based on a reflected ultrasound received from the subject;
   an image generating section which generates original image data based on the received signal acquired by said ultrasound probe;
   an output image generating section which generates output image data that has a predetermined output size by performing an image size changing process on the original image data generated by said image generating section;
   a comparison image generating section which generates comparison image data by changing an image size corresponding to the output image data generated by said output image generating section so that an image size corresponding to the comparison image data is identical to an image size corresponding to the original image data generated by said image generating section;
   an image correction section which: (i) compares the original image data generated by said image generating section with the comparison image data generated by said comparison image generating section on a pixel-by-pixel basis, and (ii) corrects the output image data generated by said output image generating section such that a difference between pixels of the comparison image data generated by said comparison image generating section and pixels of the original image data generated by said image generating section approaches zero; and
   a control section which, based on a predetermined frame rate of the ultrasound diagnostic apparatus for displaying the output image data, sets a number of times: (i) the generation of the comparison image data by said comparison image generating section, (ii) the comparison between the original image data and the generated comparison image data by said image correction section, and (iii) the correction of the output image data by said image correction section, are repeated,
   wherein the predetermined frame rate is set based on predetermined transmission/reception conditions of ultrasound including at least one of a depth of a focus point and a number of emissions of a transmission beam, and
   wherein the control section repeats the generation, the comparison, and the correction for the set number of times.

2. The ultrasound diagnostic apparatus described in claim 1, wherein said image correction section corrects the output image data by:
   a) changing processing conditions of the image size changing process performed by said output image generating section, based on the difference between pixels of the comparison image data generated by said comparison image generating section and pixels of the original image data generated by said image generating section; and
   b) controlling said output image generating section to newly generate output image data based on the changed processing conditions.

3. The ultrasound diagnostic apparatus described in claim 1, further comprising a display section which displays an image based on the output image data generated by said output image generating section;
   wherein the control section:
   a) performs a freeze control process, upon reception of a freeze operation, to maintain an image, according to a timing at which the freeze operation has been received, in a state in which the image is displayed in said display section; and b) repeats the generation, the comparison, and the correction for the set number of times, with respect to output image data of the image to be displayed in said display section according to the timing at which said freeze operation has been received.

* * * * *